(12) United States Patent
Enger et al.

(10) Patent No.: US 11,656,369 B2
(45) Date of Patent: May 23, 2023

(54) RADIATION DOSIMETER

(71) Applicant: THE ROYAL INSTITUTION FOR THE ADVANCEMENT OF LEARNING/MCGILL UNIVERSITY, Montréal (CA)

(72) Inventors: Shirin Abbasi Nejad Enger, Montreal (CA); Jack Childress, Montréal (CA); Lilian Childress, Montréal (CA); Julien Megroureche, Montréal (CA)

(73) Assignee: THE ROYAL INSTITUTION FOR THE ADVANCEMENT OF LEARNING/MCGILL UNIVERSITY, Montreal (CA)

( * ) Notice: Subject to any disclaimer, the term of this patent is extended or adjusted under 35 U.S.C. 154(b) by 149 days.

(21) Appl. No.: 17/298,743

(22) PCT Filed: Dec. 20, 2019

(86) PCT No.: PCT/CA2019/051890
§ 371 (c)(1),
(2) Date: Jun. 1, 2021

(87) PCT Pub. No.: WO2020/124266
PCT Pub. Date: Jun. 25, 2020

(65) Prior Publication Data
US 2022/0035052 A1    Feb. 3, 2022

Related U.S. Application Data

(60) Provisional application No. 62/783,599, filed on Dec. 21, 2018.

(51) Int. Cl.
G01T 1/02    (2006.01)
A61B 6/00    (2006.01)

(52) U.S. Cl.
CPC .............. *G01T 1/02* (2013.01); *A61B 6/4208* (2013.01)

(58) Field of Classification Search
CPC ........ G01T 1/02; G01T 1/1606; A61B 6/4208
See application file for complete search history.

(56) References Cited

U.S. PATENT DOCUMENTS

| 2004/0178361 A1 | 9/2004 | Fentbonne | |
| 2005/0094158 A1* | 5/2005 | Paldus | .................. G01N 21/39 356/519 |

(Continued)

OTHER PUBLICATIONS

Nguyen et al., Three-Wave fiber fabry-pérot interferometer for simultaneous measurement of temperature and water salinity of seawater, in IEEE Photoics Technology letters, vol. 23, No. Apr. 1, 2011, pp. 450-452.

(Continued)

*Primary Examiner* — Marcus H Taningco
(74) *Attorney, Agent, or Firm* — Norton Rose Fulbright Canada (57) ABSTRACT

Herein provided is a radiation dosimeter and associated systems and methods. The radiation dosimeter comprises a light source configured for producing an input optical signal; a resonant cavity coupled to the light source for receiving the input optical signal, the resonant cavity configured for containing a fluid and for producing an output optical signal from the input optical signal indicative of a radiation dose absorbed by the fluid; and a light detector coupled to the optical fiber for obtaining the output optical signal.

19 Claims, 7 Drawing Sheets

(56) References Cited

U.S. PATENT DOCUMENTS

| | | | |
|---|---|---|---|
| 2006/0257877 A1* | 11/2006 | Anderle | A61L 2/0052 |
| | | | 435/6.18 |
| 2009/0180962 A1 | 7/2009 | Black et al. | |
| 2009/0289181 A1* | 11/2009 | Wickman | G01T 1/02 |
| | | | 250/252.1 |
| 2012/0181442 A1 | 7/2012 | Prieels | |
| 2016/0041271 A1* | 2/2016 | Kahilainen | G01T 1/185 |
| | | | 250/374 |
| 2017/0003403 A1 | 1/2017 | Menichelli et al. | |
| 2018/0318609 A1* | 11/2018 | Arican | A61N 5/1075 |
| 2021/0101025 A1* | 4/2021 | Marinos | G01T 1/169 |

OTHER PUBLICATIONS

Moreno-Hernandez et al., Contactless optical fiber interferometric sensor to monitor water content in Ethan, in IEEE Sensore Journal, vol. 18, No. 8, Apr. 15, 2018, pp. 3211-3213.

Avino S et al., "Radiation dosimetry with fiber Bragg gratings", Proceedings of SPIE, IEEE, US, vol. 9157, May 22, 2014, p. 91574L1-91574L4, XP060041439.

Berghmans F et al., "Evaluation of three different optical fibre temperature sensor types for application in gamma radiation environments", Radiation and Its Effects on Components and Systems, 1997. Radecs 97. Fourth European Conference on Cannes, France Sep. 15-19, 1997, New York, NY, USA, IEEE, US, Sep. 15, 1997, pp. 424-429, XP010294430.

\* cited by examiner

RADIATION DOSIMETER

TECHNICAL FIELD

The present disclosure relates generally to radiation detection, and more particularly to ionizing radiation detection in tissues.

BACKGROUND

In certain medical procedures, including cancer treatments, ionizing radiation is directed towards a tumour or other mass in an attempt to destroy certain types of cells. One goal of such procedures is to focus the radiation so that other parts of the patient's body, such as healthy tissues, have minimal exposure to the radiation. In order to assess the success of ionizing radiation procedures, radiation dosimeters can be used to measure the amount of radiation delivered to different portions of the patient's body.

Because water reacts similarly to bodily tissue when exposed to radiation, water-based radiation dosimeters represent one type of known radiation dosimeter. However, existing water-based dosimeters are typically quite large, on the order of centimeters or more, and are not easily used in vivo. Smaller dosimeters, using silicon diodes and the like, are also known, and operate on millimeter-scale. However, silicon-based dosimeters require complex correction factors to produce tissue-equivalent dosage readings.

Therefore, there is a need for improved radiation dosimeters.

SUMMARY

In accordance with a broad aspect, there is provided a radiation dosimeter, comprising: a light source configured for producing an input optical signal; an optical fiber coupled to the light source for receiving the input optical signal, the optical fiber comprising an optical cavity disposed therein, the optical cavity configured for containing a fluid and including an optical resonator to produce an output optical signal from the input optical signal; and a light detector coupled to the optical fiber for receiving the output optical signal; wherein the output optical signal is indicative of a radiation dose absorbed by the fluid.

In accordance with another broad aspect, there is provided a radiation dosimeter and associated systems and methods. The radiation dosimeter comprises a light source configured for producing an input optical signal; a resonant cavity coupled to the light source for receiving the input optical signal, the resonant cavity configured for containing a fluid and for producing an output optical signal from the input optical signal indicative of a radiation dose absorbed by the fluid; and a light detector coupled to the optical fiber for obtaining the output optical signal.

In some embodiments, the optical cavity is a resonant cavity comprising two reflective surfaces opposite each other.

In some embodiments, the reflective surfaces are spaced 10 to 300 microns apart.

In some embodiments, the two reflective surfaces each comprise a plurality of alternating layers of $SiO_2$ and $Ta_2O_5$.

In some embodiments, the optical cavity is a bottle resonator.

In some embodiments, the optical cavity is a Fabry-Perot cavity.

In some embodiments, the resonant cavity comprises a plurality of mirrors.

In some embodiments, the fluid is water.

In some embodiments, the fluid is a solution of water and sodium hydroxide.

In some embodiments, at least a portion of the optical fiber including the optical cavity is configured to be received within a body of a patient.

In some embodiments, the radiation dosimeter further comprises an analysis module communicatively coupled with the light detector, the analysis module operable to determine the radiation dose absorbed by the fluid based on the output optical signal captured by the light detector.

In accordance with another broad aspect, there is provided a radiation dosimeter system, comprising: a radiation dosimeter according as described hereinabove; and a radiation source for producing the radiation dose.

In some embodiments, the ionization source is a particle accelerator.

In some embodiments, the ionization source is a laser-light source.

In accordance with a further broad aspect, there is provided a method for performing radiation dosimetry, comprising: emitting an input optical signal into an optical fiber; obtaining, from the optical fiber, an output optical signal produced by an optical cavity formed in the optical fiber, the optical cavity configured for containing a fluid; and determining, based on the output optical signal, a radiation dose present in the fluid.

In some embodiments, the method further comprises placing a fluid in the resonant cavity.

In some embodiments, the fluid is water or an aqueous solution.

In some embodiments, the method further comprises ionizing the fluid with an ionization source.

In some embodiments, the method further comprises placing at least a portion of the optical fiber including the resonant cavity within a body of a patient.

Features of the systems, devices, and methods described herein may be used in various combinations, in accordance with the embodiments described herein.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Figure 1:
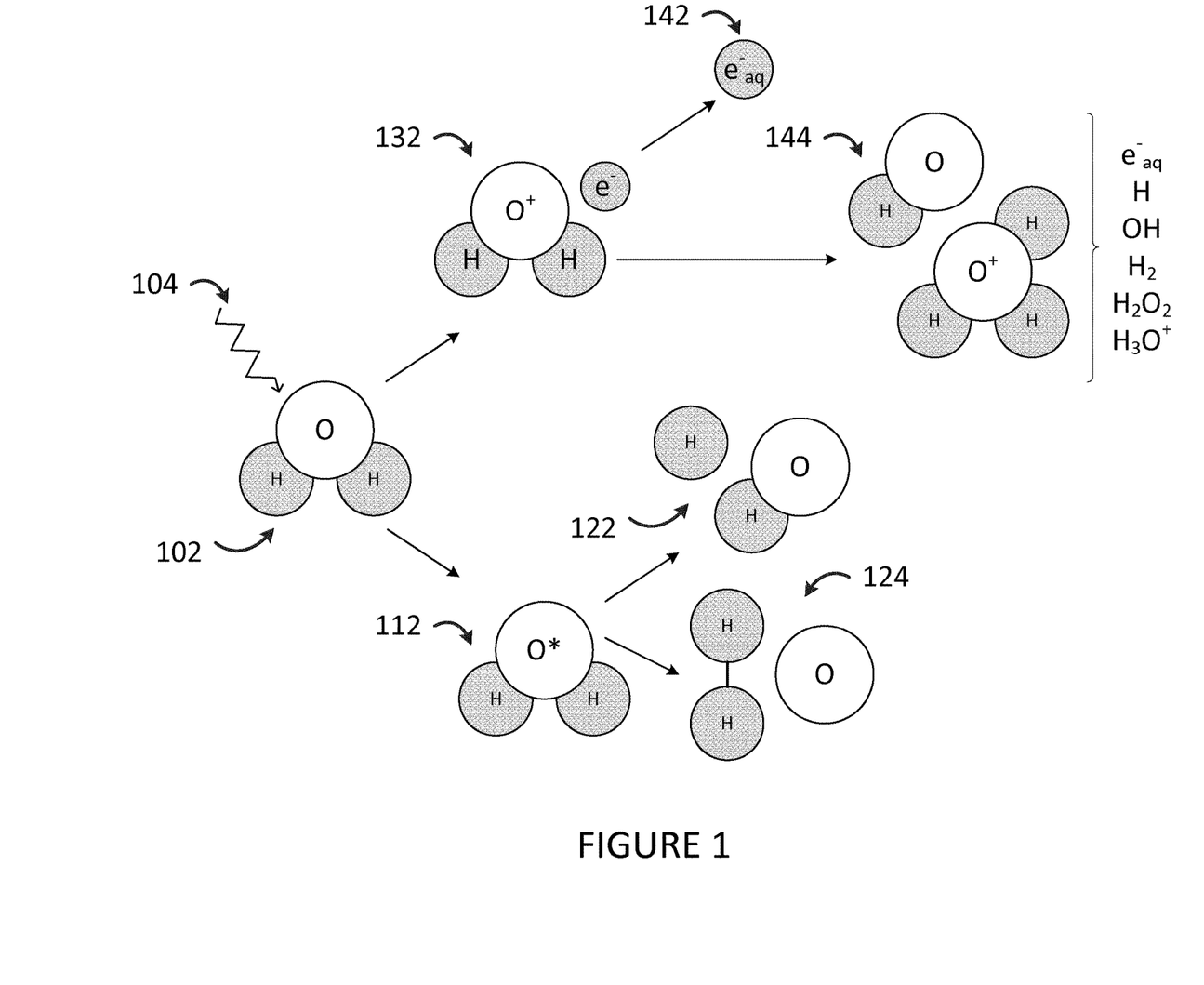
FIG. 1 is a diagram of example products of water radiolysis.

By way of introduction, and with reference to FIG. 1, exposure to ionizing radiation can cause water molecules to decompose in a variety of different ways. Shown at 102 is a generic water ($H_2O$) molecule, on which is incident ionizing radiation 104. As used herein, the terms "ionizing radiation" and "radiation" are synonymous, and can refer to any suitable type of radiation which produces ionization in the medium through which it passes, including X-rays, gamma rays, α-particle radiation, β-particle radiation, heavy ions, light of various types, including laser light, and the like. It should also be noted that other decomposition pathways, in addition to those described herein, are also possible, and considered within the scope of the present disclosure.

A first decomposition pathway consists in the production of excited water ($H_2O^*$) at 112, which in turn decomposes into a lone hydrogen radical (H) and a hydroxide ion (OH) at 122, or into dihydrogen ($H_2$) and a lone oxygen radical (O) at 124. A second decomposition pathway consists in the production of a free electron ($e^-$) and ionized water ($H_2O^+$) at 132. The free electron can recombine with the aqueous solution ($e_{aq}^-$), shown at 142, and the ionized $H_2O^+$ can produce a variety of compounds at 144, including OH ions, hydronium ($H_3O^+$), hydrogen peroxide ($H_2O_2$), and the like.

The presence of hydrated electrons in water produces dipole orientation in water molecules, which in turn causes the electron to be trapped in a positive potential well. As a result, the presence of hydrated electrons in water produces a change in the optical absorption spectrum of water for light having a wavelength of approximately 700 nm, or a frequency on the order of 400 THz. In some cases, the extinction coefficient for light having a wavelength of 700 nm is approximately $1.85 \times 10^3$ $m^2 \cdot mol^{-1}$. Similar principles apply for other aqueous solutions.

Figure 2A:
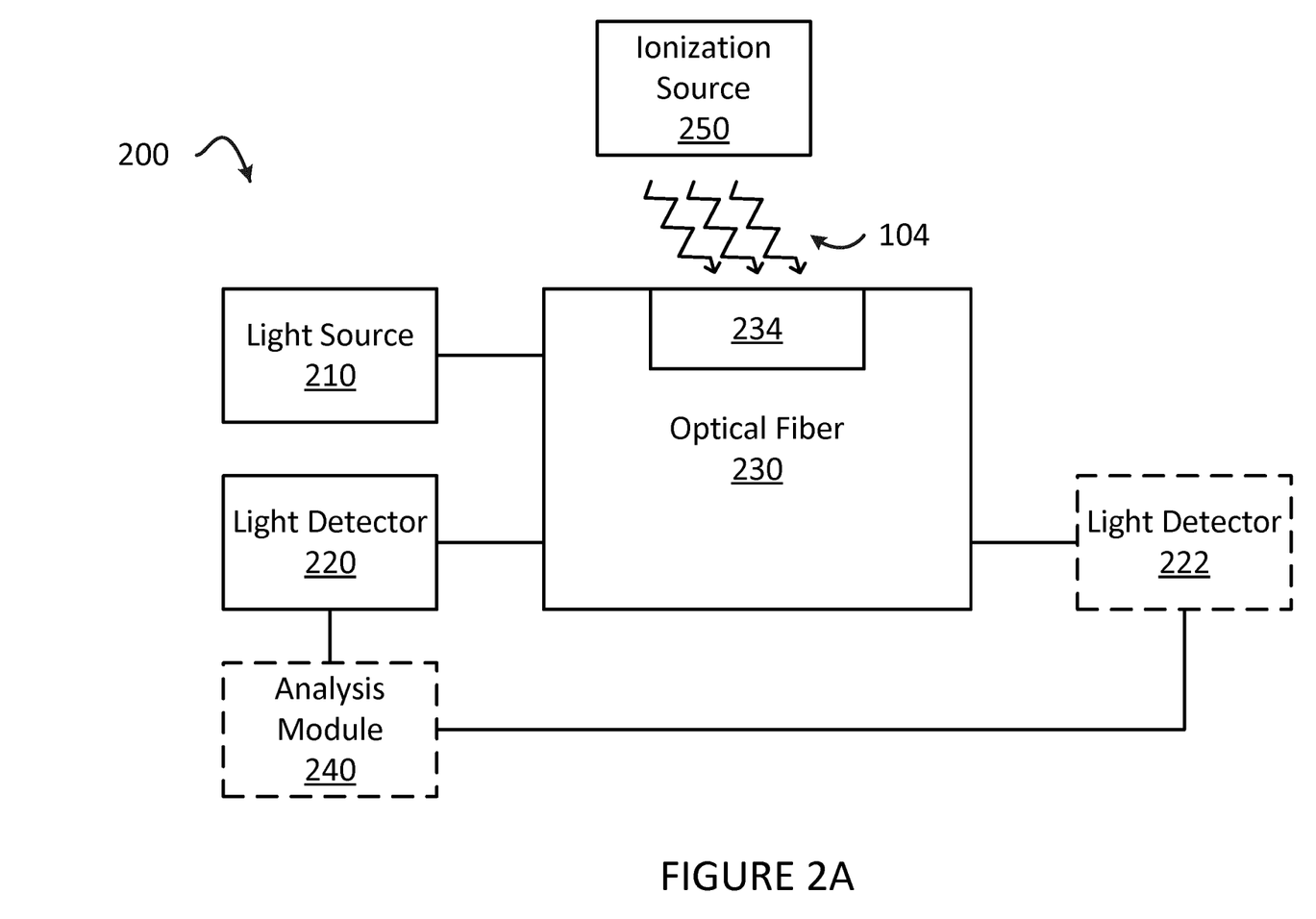
FIGS. 2A-B are block diagrams of example radiation dosimeters.

With reference to FIG. 2A, a radiation dosimeter 200 which operates based on at least some of the aforementioned principles will now be described. The dosimeter 200 is composed of a light source 210, a light detector (or simply "detector") 220, and an optical fiber 230. The radiation dosimeter 200 serves to measure a quantity of radiation 104 produced, for example, by an ionization source 250, which can be any suitable type of particle accelerator, including a linear particle accelerator, for instance as used in medical or industrial settings. It should be noted that the radiation 104 produced by the accelerator 250 can be produced in a pulsed manner, a substantially continuous manner, or in any other fashion. Other ionization sources are also considered, for instance brachytherapy radiation sources, laser-light based systems, or any other suitable source of radiation. The radiation dosimeter 200 and the ionization source 250 can together form a radiation dosimeter system.

The light source 210 is configured for emitting an input optical signal into the optical fiber 230, which then travels through the optical fiber. As described in greater detail hereinbelow, the optical fiber 230 includes an optical cavity 234, through which the input optical signal transits and which produces an output optical signal based on the input optical signal from the light source 210. The optical cavity 234 can be any suitable type of resonant optical cavity, that is to say which produces a resonance effect within the optical cavity. The optical cavity 234 can be embodied as a bottle resonator, a Fabry-Perot cavity, or any other suitable optical cavity. The optical cavity 234 can be disposed within the optical fiber 230 in any suitable fashion, and at any suitable location.

The optical cavity 234 is configured for producing the output optical signal based on the input optical signal from the light source 210, which can be either a reflected output optical signal or a transmitted output optical signal. In some embodiments, including as illustrated in FIG. 2A, the detector 220 can be located at the same end of the optical fiber 230 as the light source 210 for detecting a reflected output optical signal produced by the optical cavity 234, which can be, for example, a resonant cavity. In other embodiments, a detector can be located at the opposite end of the optical fiber 230 as the light source 210, as illustrated by light detector 222. The detector 222 can detect a transmitted output optical signal produced by the optical cavity 234 and which exits the optical fiber 230 at the end opposite that at which the input optical signal entered. In these embodiments, the optical cavity 234 can be, for example, a bottle resonator or a Fabry-Perot cavity, or any other suitable cavity which, in some embodiments, can be used to amplify a signal, as described in greater detail hereinbelow.

The light source 210 and detector 220 can be any suitable devices for producing and receiving optical signals, respectively. The light source 210 is configured for producing light of any suitable wavelength or frequency, at any suitable intensity, and according to any suitable pattern. In some embodiments, the light source 210 produces a substantively continuous input optical signal. In other embodiments, the light source 210 produces a plurality of light pulses which constitute the input optical signal. Still other embodiments are considered. In addition, in some embodiments the input optical signal, produced by the light source 210, can be modulated to encode particular information, for instance a timestamp indicative of a moment at which the input optical signal was produced, or any other suitable information.

The detector 220 obtains and detects the output optical signal in any suitable manner. The detector is configured for obtaining and detecting light of any suitable wavelength or frequency, and for characterizing obtained light, including the output optical signal, in any suitable fashion. For example, the detector can characterize the intensity, bandwidth, and/or pattern of the output optical signal, and in some embodiments is configured for demodulating the output optical signal to obtain the information encoded in the input optical signal transmitted by the light source 210.

As discussed in greater detail hereinbelow, the optical cavity 234 is configured for trapping the input optical signal, which is produced by the light source 210, and for producing the output optical signal, which is obtained by the detector 220. Additionally, the optical cavity 234 is configured for receiving a fluid, for example water, or any other aqueous solution. In some embodiments, the fluid is pure water, that is to say, water substantially free of additives. In other embodiments, the fluid is an aqueous solution which includes various additives to water, for example to mimic or resemble the response of human tissue. For instance, the aqueous solution includes sodium hydroxide (NaOH), or any other suitable compound or chemical. The aqueous solution can have dissolved therein various chemicals, cells or cell components, and the like, to tailor the response of the aqueous solution to the input optical signal.

Depending on the composition of the fluid, characteristics of the output optical signal can vary. For example, if the fluid exhibits an optical absorption spectrum which has a high extinction coefficient for light at the same wavelength as that of the input optical signal transmitted by the light source 210, the fluid in the optical cavity 234 can cause the output optical signal to have a reduced intensity compared to the intensity of the input optical signal. Other examples, in which other fluids produce other effects in the output optical signal, are also considered. For example, fluids in the optical cavity 234 can cause a phase shift in the output optical signal vis-à-vis the input optical signal, a change in the resonant frequency of the optical cavity 234, which in turn can result in a change in intensity and in phase, or the like.

In a particular example, the fluid in the optical cavity 234 is water, water-based, any other suitable aqueous solution, or any water-like or aqueous-like solution. The incidence of radiation 104 on the fluid in the optical cavity 234 can produce hydrated electrons in the fluid, which can increase the extinction coefficient of the fluid for light having a wavelength of approximately 700 nm, as discussed above. Thus, if the input optical signal produced by the light source 210 has a wavelength of approximately 700 nm, the attenuation in the output optical signal, produced by the presence of the fluid in the optical cavity 234, can be indicative of the amount of radiation to which the fluid was exposed.

Optionally, the radiation dosimeter 200 includes an analysis module 240, which is communicatively coupled to the detector 220 for receiving therefrom information relating to the characterization of the output optical signal performed by the detector 220. The analysis module 240 is configured for analyzing the output optical signal as characterized by the detector 220, for example to determine the dose of radiation absorbed by the fluid. In some embodiments, the functionality of the analysis module is incorporated into the detector 220, which can be configured for producing an indication of the amount of radiation absorbed by the fluid.

In some embodiments, the analysis module 240 is configured for evaluating an absorbed dose of radiation for the fluid in the optical cavity 234. The analysis module 240, or the detector 220, can implement the following equation:

$$D = 9.65 \times 10^8 \cdot \frac{OD}{\rho \cdot \epsilon \cdot \ell \cdot G(e_{aq}^-)} \quad (1)$$

where D is an absorbed dose of radiation (in centigray), OD is an absorption optical density for the optical cavity 234, $\rho$ is the physical density of the fluid (which is approximately 1 in water or aqueous solutions), $\epsilon$ is the molar extinction coefficient of the fluid (in liter per mole per centimeter), $\ell$ is the optical path length of the optical cavity 234 (in centimeter), and $G(e_{aq}^-)$ is a hydrated electron yield (in moles per electron-volt), for example relative to the radiation chemical yield. In this equation, the factor $9.65 \times 10^8$ serves for unit conversion.

The absorption optical density for the optical cavity 234 (OD) can be expressed as a log ratio of the intensity of the input optical signal and the intensity of the output optical signal:

$$OD = \log_{10} \frac{I_o}{I} \quad (2)$$

where $I_o$ is the intensity of the input optical signal, and I is the intensity of the output optical signal.

The hydrated electron yield $G(e_{aq}^-)$ in equation (1) can vary based on a number of factors, including the linear energy transfer (LET) of the radiation 104, the pH of the fluid contained in the optical cavity 234, the concentration of so-called scavenger molecules in the fluid, which can include $OH^-$ and $H_3O^+$ ions, $H_2$, and sodium hydroxide (NaOH), and the concentration of hydrated electrons in the fluid.

It should be noted that the absorption-based techniques described hereinabove are but one approach which can be used to determine the absorbed dose of radiation for the fluid in the optical cavity 234. In some other embodiments, other optical approaches, including cavity ring-down spectroscopy, or reflection-based approaches, are employed. For instance, optical approaches which provide a suitably-rapid response time for transient signals can be employed.

Figure 2B:
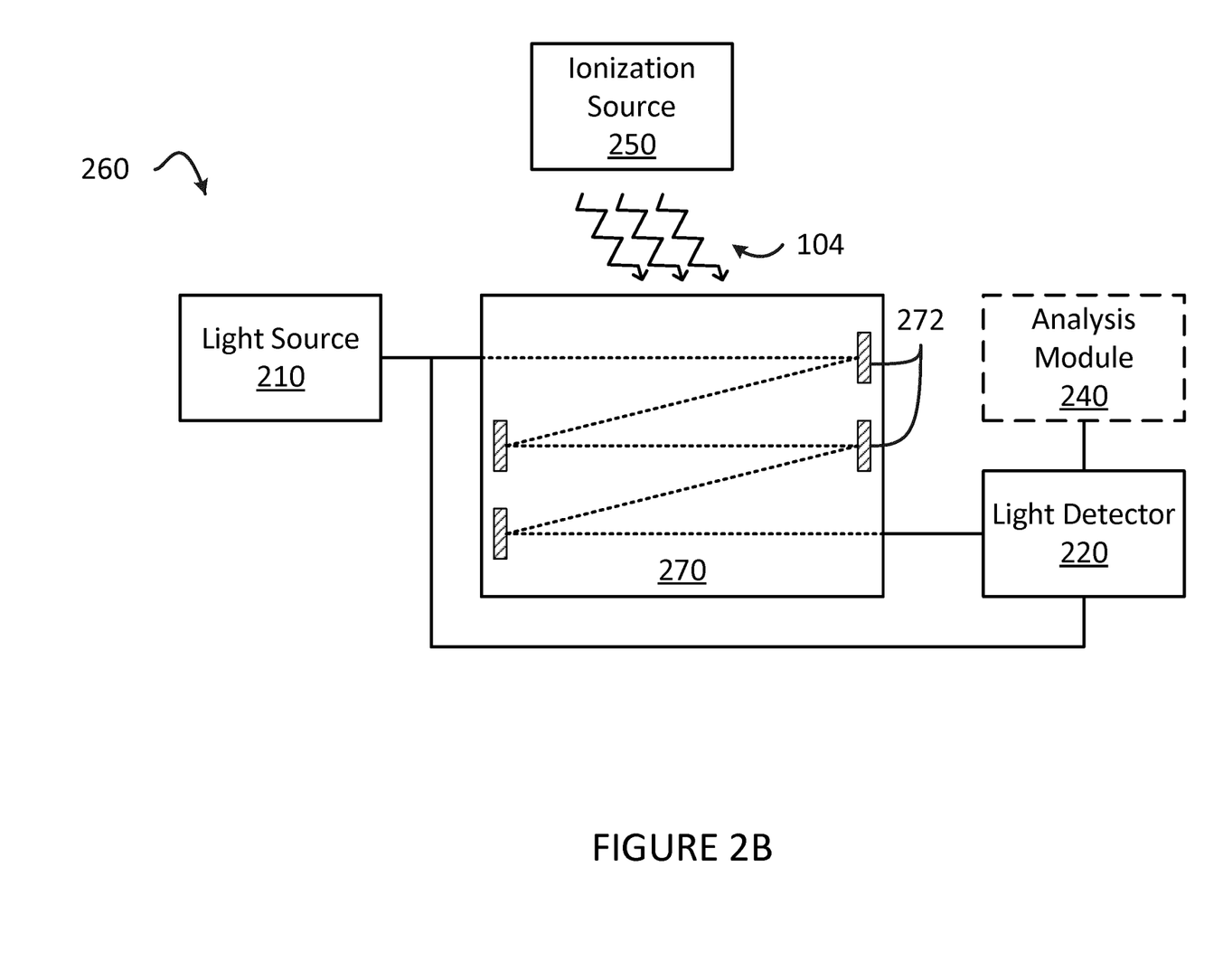

With reference to FIG. 2B, an alternative embodiment of a radiation dosimeter is illustrated at 260, in which optical fiber 230 with the optical cavity 234 of the radiation dosimeter 200 is replaced with a resonator 270. The light source 210 emits the input optical signal into the resonator 270, for instance via one or more optical fibers. The resonator 270 is a vessel or other container in which a fluid, for instance water, is held, and in which is disposed a plurality of reflective elements, illustrated here as mirrors 272. The mirrors 272 reflect the input optical signal at least once through the resonator 270, in order to lengthen the effective optical path travelled by the input optical signal through the fluid contained in the resonator 270. The resonator 270 can be of any suitable shape and size, and contain any suitable number of mirrors 272, or of any other suitable type of reflective elements. In some embodiments, the effective optical path travelled by the input optical signal is on the order of several meters.

The input optical signal then exits the resonator 270 and is received by the detector 220, which characterizes the intensity, bandwidth, and/or pattern of the output optical signal, and in some embodiments is configured for demodulating the output optical signal to obtain the information encoded in the input optical signal transmitted by the light source 210, optionally using the analysis module 240, as described hereinabove. Other embodiments are also considered. It should be noted that the connections between the resonator 270 and the various other components of the radiation dosimeter 260 can be implemented using various optical fiber cables, as appropriate.

In some cases, the radiation dosimeter 260 can be used to produce much longer effective optical paths, for instance on the order of several tens or hundreds of meters, and can be used for testing and/or verification purposes. For instance, the radiation dosimeter 260 can be used to test beam generators or other light sources, for instance to assess the quality of the produced laser beam.

In one example implementation, the resonator 270 is implemented with a 60 cm optical path and is filled with deionized pure water. A 45 mW laser diode, having a wavelength of 660 nm, is used as the light source 210, and biased silicon photodetectors are used as the light detector 220. A Varian Truebeam™ linear accelerator is used to irradiate the water in the resonator 270 with 10 MV of flattening-filter-free (FFF) photons. Absorption of the input optical signal produced by the laser diode can be monitored with the photodetectors to measure the absorbed dose of radiation for the fluid in the resonator 270.

Figure 3A:
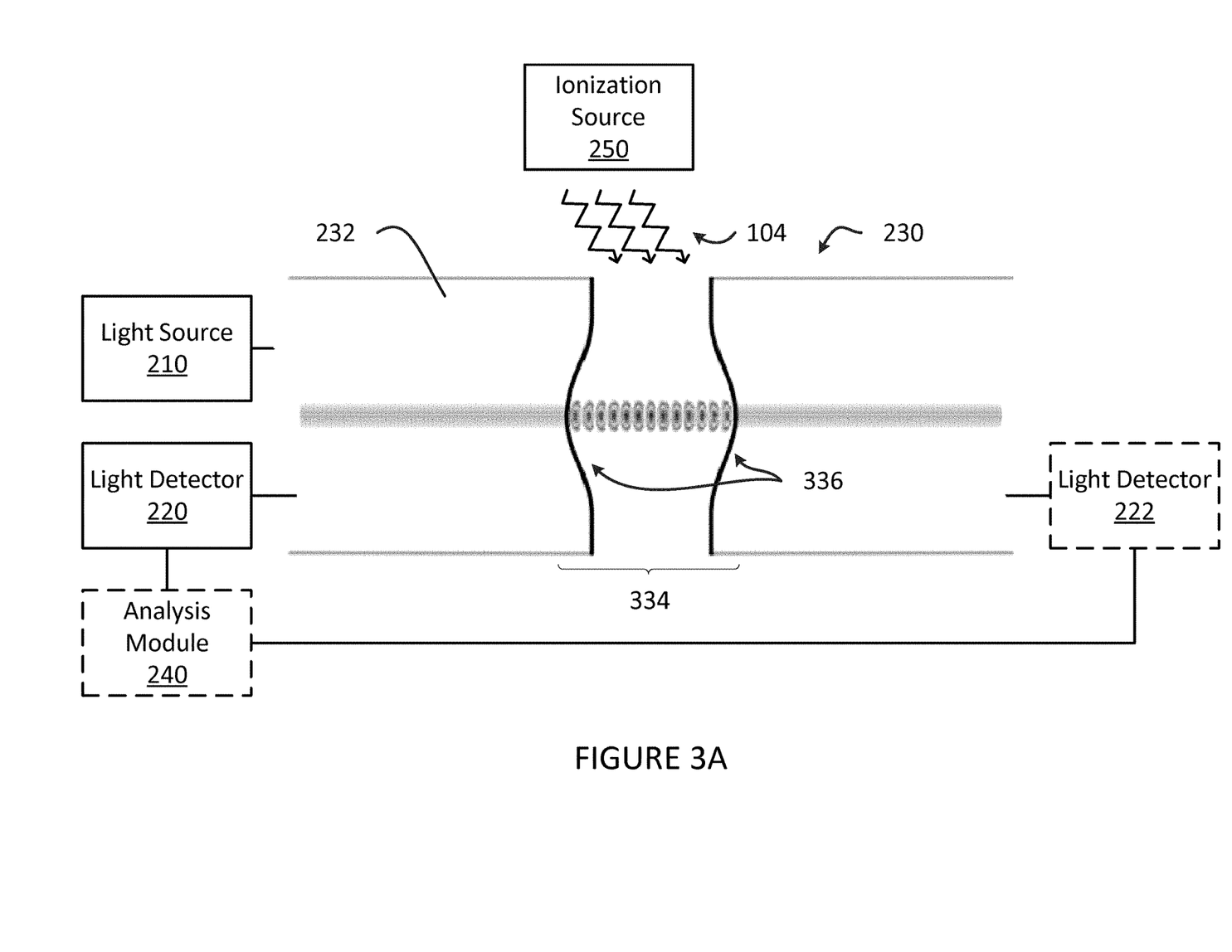
FIGS. 3A-B are schematic diagrams of example optical fibers for use with the radiation dosimeters of FIG. 2A and/or 2B.

With reference to FIG. 3A, due to the nature of the absorption effect, in some embodiments the optical path length $\ell$ in equation (1) would need to be on the order of meters in order for the absorption effect to be measurable. In some embodiments, in order to produce a suitable optical path length $\ell$ while minimizing the size of the optical cavity, a resonant cavity 334 is provided via reflective surfaces 336 which bound the resonant cavity 334. The reflective surfaces together form the resonant cavity. In embodiments in which another type of optical cavity is used, other implementations are considered.

The resonant cavity 334 can be machined into, or otherwise formed within, the optical fiber 230 and bounded by transmission portions 232 of the optical fiber 230. In some embodiments, the resonant cavity 334 is formed using laser-based techniques, which can include laser cleaving, laser ablation, and the like. Other techniques are also considered. The reflective surfaces 336 can be formed and/or deposited on the ends of the resonant cavity 334 using any suitable technique. In some embodiments, the reflective surfaces 336 consist of alternating layers of silicon dioxide ($SiO_2$) and tantalum pentoxide ($Ta_2O_5$), although other compositions are also considered. Such material layers formed on the internal surfaces of the resonant cavity 334 in order to form the reflective surfaces 336 may be applied by a suitable coating and/or deposition processing, including atomic layer deposition, electron beam evaporation, ion-assisted deposition, ion plating, magnetron sputtering, ion beam sputtering, and the like.

The reflective surfaces 336 of the resonant cavity 334 produce an effective optical path length $\ell$ orders of magnitude longer than the actual length of the resonant cavity 334. For example, the resonant cavity 334 can have a width of a few microns (μm), for instance between 10 and 300 microns, and produce an effective optical path length $\ell$ on the order of meters. When the input optical signal enters the cavity, it is "trapped" by the reflective surfaces 336, causing the input optical signal to perform hundreds or thousands of "round-trips" between the reflective surfaces 336 before exiting the resonant cavity 334. In some embodiments, the input optical signal performs over 100,000 round-trips before exiting the resonant cavity 334. In some embodiments, the use of the resonant cavity 334 can result in higher resolutions for transient signals.

Figure 3B:
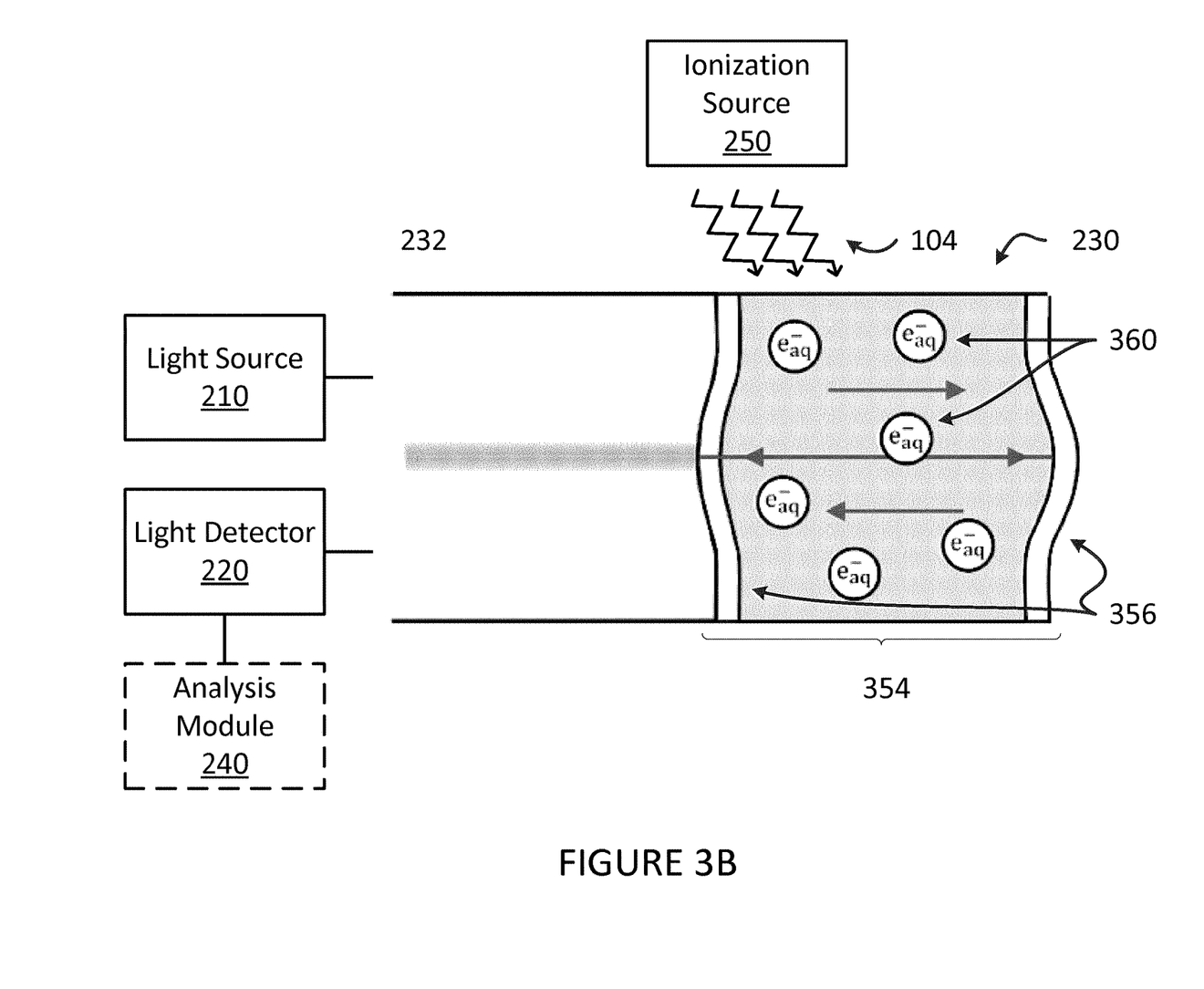

With reference to FIG. 3B, there is illustrated an alternative embodiment of the optical fiber 230 which has disposed therein a resonant cavity 354, formed by reflective surfaces 356. The reflective surfaces 356 are composed of similar material as the reflective surfaces 336, but the farther reflective surface 356 (i.e., farther from the light source 210) is substantially impermeable, and the light from input optical signal can exit the resonant cavity 354 via the nearer reflective surface only, thereby forming the output optical signal As illustrated in FIG. 3B, the resonant cavity 354 is filled with a fluid which contains aqueous electrons 360 (denoted with $e_{aq}^-$). The fluid can be any suitable type of fluid, including water, water-based solutions, and the like. The fluid and the resonant cavity 354 can serve to amplify the input optical signal to produce the output optical signal, as discussed hereinabove.

With additional reference to FIG. 2A, as discussed hereinabove, the optical cavity 234 and the resonant cavity 334 are configured for receiving a fluid, which is contained within the cavities 234, 334, for instance between the reflective surfaces 336, such that the input optical signal provided by the light source 210 is transmitted through the fluid, reflected between the reflective surfaces 336, and then output through the transmission portions 232 of the optical fiber 230, toward the detector 220 and/or the detector 222. The input optical signal is transmitted through the fluid hundreds or thousands of times before exiting the optical cavity 234 or the resonant cavity 334, which can increase the light extinction effect caused by the fluid in the optical cavity 234 or the resonant cavity 334.

It should be noted that in some embodiments, the transmission portions 232 of the optical fiber 230 can be substantially separate from the optical cavity 234. In these embodiments, the optical cavity 234 is configured for being coupled to the transmission portions 232 of the optical fiber 230 in any suitable fashion.

In some embodiments, the reflective surfaces 336 are provided as having different reflection coefficients. For example, a first one of the reflective surfaces 336 can be substantially perfectly reflective, and a second one of the reflective surfaces 336 can have a finite reflectivity. For instance, the reflective surface 336 most distant from the detector can have a substantially perfect reflectivity, and the reflective surface most proximate the detector 220 can have a finite reflectivity.

In some embodiments, the accelerator 250 or other radiative device is used to produce the radiation 104, which in turn produces the hydrated electrons present in the fluid. The radiation 104 can be produced as a series of pulses of radiation. The time duration of the pulses can be selected such that it is a duration negligible compared to the half-life of the hydrated electrons present in the fluid. For example, if the half-life of the hydrated electrons is on the order of 200 μs (in pure water), the pulse lengths can be one or more orders of magnitude shorter than 200 μs. In addition, the rise and fall time of the pulses should be negligible compared to the length of the pulse. The accelerator 250 can produce pulses of any suitable length and intensity for generating hydrated electrons of a suitable concentration for detection within the optical cavity 234. Other approaches are also considered.

Using the optical fiber 230, with the optical cavity 234 or the resonant cavity 334, it is possible to produce an embodiment of the radiation dosimeter 200 which can be used on a micron scale. In some embodiments, the radiation dosimeter 200 is configured for in vivo application, that is to say for use in a body of a patient, for example a patient receiving a radiation treatment. The optical cavity 234 or the resonant cavity 334 can be inserted into a portion of the body of the patient which is to be subjected to a radiation treatment, or which is proximate to a portion of the body of the patient which is to be subjected to a radiation treatment.

When so inserted, the optical cavity 234 or the resonant cavity 334, which is filled with water or another an aqueous solution, reacts to the absorption of radiation similar to tissues in the body. The amount of radiation absorbed by the fluid will produce the light extinction effect described hereinabove, or another optical effect, when the input optical signal is provided from the source to the optical fiber 230. In this fashion, the radiation dosimeter 200 can be used to measure the amount of radiation to which the portion of the body is exposed, based on the output optical signal obtained by the detector 220. It should be noted that the transmission portion 232 of the optical fiber 230 can be outside the body of the patient, in order to couple with the light source 210 and the detector 220. It should additionally be noted that the techniques disclosed herein can also be implemented for ex vivo applications.

In some embodiments, radiochromic films can be positioned with the optical cavity 234, the resonator 270, the resonant cavity 334, and/or the resonant cavity 354. The radiochromic films can serve to calibrate the cavity or resonator in which it is inserted. The radiochromic films could serve in other embodiments as well.

Figure 4:
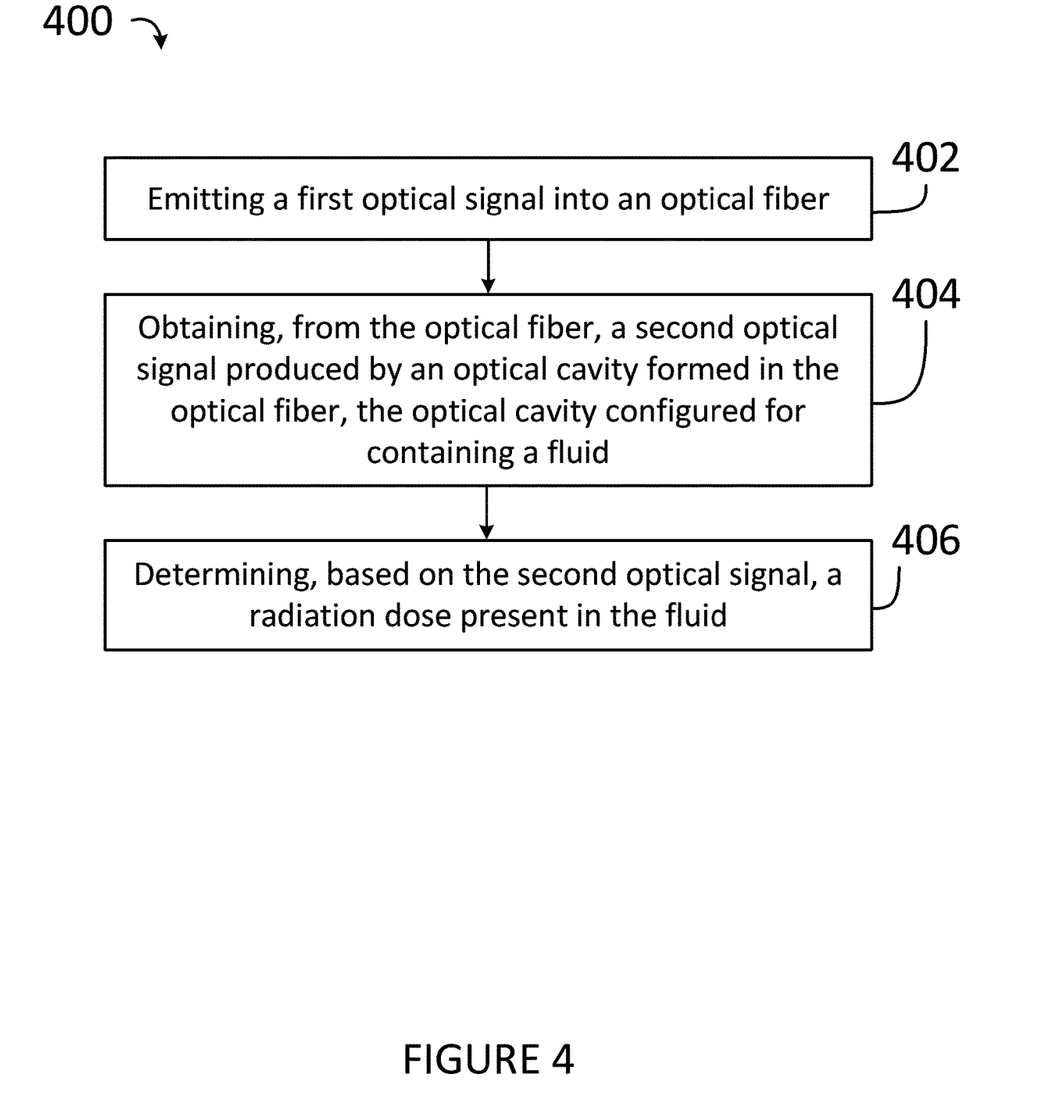
FIG. 4 is a flowchart of an example method for determining a radiation dose.

With reference to FIG. 4, a method 400 for performing radiation dosimetry is described. At step 402, an input optical signal is emitted into an optical fiber, for example the optical fiber 230. The optical fiber can have defined therein an optical cavity, for example the resonant cavity 334, with reflective surfaces 336.

At step 404, an output optical signal is obtained from the optical fiber 230. The output optical signal is produced by the resonant cavity 334, which is configured for containing a fluid, and can be produced via the reflective surfaces 336. The characteristics of the output optical signal are affected by the nature of the fluid in the resonant cavity 334.

At step 406, a radiation dose absorbed by the fluid is determined based on the output optical signal. For example, the radiation dose can be determined using the equations (1) and (2) described hereinabove. In some embodiments, other information, for instance the dimensions of the resonant cavity 334, the reflectivity of the reflective surfaces 336, and the like, are also used to determine the radiation dose.

Figure 5:
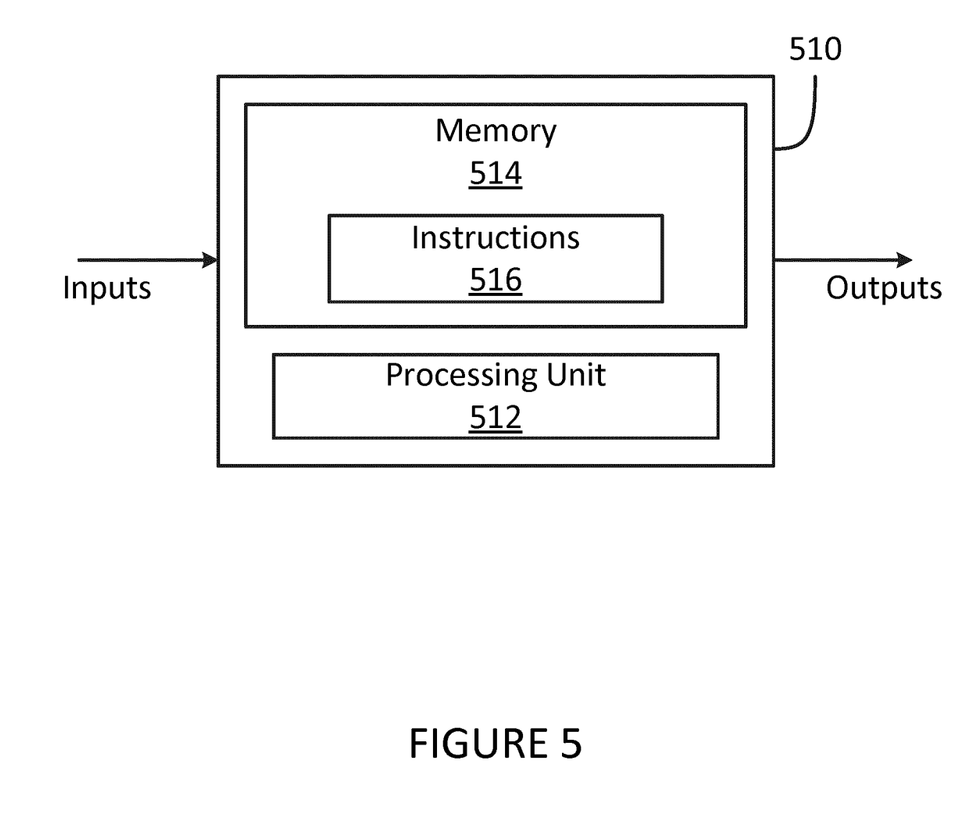
FIG. 5 is a schematic diagram of a computing system for implementing the method of FIG. 4, in accordance with an embodiment.

With reference to FIG. 5, the method 400 may be implemented, at least in part, via a computing device 510, comprising a processing unit 512 and a memory 514 which has stored therein computer-executable instructions 516. The processing unit 512 may comprise any suitable devices configured to implement the method 400 such that instructions 516, when executed by the computing device 510 or other programmable apparatus, may cause the functions/acts/steps of the method 400 described herein to be executed. The processing unit 512 may comprise, for example, any type of general-purpose microprocessor or microcontroller, a digital signal processing (DSP) processor, a central processing unit (CPU), an integrated circuit, a field programmable gate array (FPGA), a reconfigurable processor, other suitably programmed or programmable logic circuits, or any combination thereof.

The memory 514 may comprise any suitable known or other machine-readable storage medium. The memory 514 may comprise non-transitory computer readable storage medium, for example, but not limited to, an electronic, magnetic, optical, electromagnetic, infrared, or semiconductor system, apparatus, or device, or any suitable combination of the foregoing. The memory 514 may include a suitable combination of any type of computer memory that is located either internally or externally to device, for example random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like. Memory 514 may comprise any storage means (e.g., devices) suitable for retrievably storing machine-readable instructions 516 executable by processing unit 512.

For example, the analysis module 240 can be implemented via the computing device 510. Alternatively, or in addition, a control system which controls the operation of the light source 210 and the detector 220 can be implemented via the computing device 510. In some embodiments, a single computing device, such as the computing device 510, can be used to implement the analysis module 240 and the control system. In other embodiments, separate computing devices 510 are provided for each of the analysis module 240 and the control system.

The methods and systems associated with the radiation dosimeter described herein may be implemented in a high level procedural or object oriented programming or scripting language, or a combination thereof, to communicate with or assist in the operation of a computer system, for example the computing device 510. Alternatively, the methods and systems described herein may be implemented in assembly or machine language. The language may be a compiled or interpreted language. Program code for implementing the methods and systems described herein may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems described herein may also be considered to be implemented by way of a non-transitory computer-readable storage medium having a computer program stored thereon. The computer program may comprise computer-readable instructions which cause a computer, or more specifically the processing unit 512 of the computing device 510, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The above description is meant to be exemplary only, and one skilled in the relevant arts will recognize that changes may be made to the embodiments described without departing from the scope of the invention disclosed. For example, the blocks and/or operations in the flowcharts and drawings described herein are for purposes of example only. There may be many variations to these blocks and/or operations without departing from the teachings of the present disclosure. For instance, the blocks may be performed in a differing order, or blocks may be added, deleted, or modified. While illustrated in the block diagrams as groups of discrete components communicating with each other via distinct data and/or optical signal connections, it will be understood by those skilled in the art that the present embodiments are provided by a combination of hardware and software components, with some components being implemented by a given function or operation of a hardware or software system, and many of the data paths illustrated being implemented by data communication within a computer application or operating system. The structure illustrated is thus provided for efficiency of teaching the present embodiment.

The present disclosure may be embodied in other specific forms without departing from the subject matter of the claims. Also, one skilled in the relevant arts will appreciate that while the systems, methods and computer readable mediums disclosed and shown herein may comprise a specific number of elements/components, the systems, methods and computer readable mediums may be modified to include additional or fewer of such elements/components. The present disclosure is also intended to cover and embrace all suitable changes in technology. Modifications which fall within the scope of the present invention will be apparent to those skilled in the art, in light of a review of this disclosure, and such modifications are intended to fall within the appended claims.

The invention claimed is:

1. A radiation dosimeter, comprising:
a light source configured for producing an input optical signal;
a resonant cavity coupled to the light source for receiving the input optical signal, the resonant cavity configured for containing a fluid and for producing an output optical signal from the input optical signal indicative of a radiation dose absorbed by the fluid; and a light detector coupled to the resonant cavity for receiving the output optical signal.

2. The radiation dosimeter of claim 1, wherein the resonant cavity comprising two reflective surfaces opposite each other.

3. The radiation dosimeter of claim 2, wherein the reflective surfaces are spaced 10 to 300 microns apart.

4. The radiation dosimeter of claim 2, wherein the two reflective surfaces each comprise a plurality of alternating layers of $SiO_2$ and $Ta_2O_5$.

5. The radiation dosimeter of claim 1, wherein the resonant cavity is a bottle resonator.

6. The radiation dosimeter of claim 1, wherein the resonant cavity is a Fabry-Perot cavity.

7. The radiation dosimeter of claim 1, wherein the resonant cavity comprises a plurality of mirrors.

8. The radiation dosimeter of claim 1, wherein the fluid is water.

9. The radiation dosimeter of claim 1, wherein the fluid is a solution of water and sodium hydroxide.

10. The radiation dosimeter of claim 1, wherein at least a portion of the resonant cavity is configured to be received within a body of a patient.

11. The radiation dosimeter of claim 1, further comprising an analysis module communicatively coupled with the light detector, the analysis module operable to determine the radiation dose absorbed by the fluid based on the output optical signal captured by the light detector.

12. A radiation dosimeter system, comprising:
the radiation dosimeter according to claim 1; and
an ionization source for producing the radiation dose.

13. The radiation dosimeter system of claim 12, wherein the ionization source is a particle accelerator.

14. The radiation dosimeter system of claim 12, wherein the ionization source is a laser-light source.

15. A method for performing radiation dosimetry, comprising:
emitting an input optical signal into a resonant cavity;
obtaining, from the resonant cavity, an output optical signal, the resonant cavity configured for containing a fluid; and
determining, based on the output optical signal, a radiation dose present in the fluid.

16. The method of claim 15, further comprising placing a fluid in the resonant cavity.

17. The method of claim 16, wherein the fluid is water or an aqueous solution.

18. The method of claim 16, further comprising ionizing the fluid with an ionization source.

19. The method of claim 15, further comprising placing at least a portion of an optical fiber including the resonant cavity within a body of a patient.

* * * * *